United States Patent
Sullivan et al.

(10) Patent No.: US 10,918,879 B2
(45) Date of Patent: Feb. 16, 2021

(54) WEARABLE CARDIOVERTER DEFIBRILLATOR (WCD) SYSTEM REACTING TO HIGH-AMPLITUDE ECG NOISE

(71) Applicant: West Affum Holdings Corp., Grand Cayman (KY)

(72) Inventors: Joseph Leo Sullivan, Kirkland, WA (US); Jaeho Kim, Redmond, WA (US)

(73) Assignee: West Affum Holdings Corp., Grand Cayman (KY)

( * ) Notice: Subject to any disclaimer, the term of this patent is extended or adjusted under 35 U.S.C. 154(b) by 109 days.

(21) Appl. No.: 16/038,007

(22) Filed: Jul. 17, 2018

(65) Prior Publication Data

US 2019/0030352 A1    Jan. 31, 2019

Related U.S. Application Data

(60) Provisional application No. 62/538,145, filed on Jul. 28, 2017.

(51) Int. Cl.
*A61N 1/39* (2006.01)
*A61N 1/04* (2006.01)
(Continued)

(52) U.S. Cl.
CPC ......... *A61N 1/3987* (2013.01); *A61N 1/0484* (2013.01); *A61N 1/3904* (2017.08);
(Continued)

(58) Field of Classification Search
CPC ............... A61N 1/3987; A61N 1/3904; A61N 1/39046; A61N 1/0484; A61N 1/3975;
(Continued)

(56) References Cited

U.S. PATENT DOCUMENTS

| 3,724,355 A | 4/1973 | Unger |
|---|---|---|
| 4,583,524 A | 4/1986 | Hutchins |

(Continued)

FOREIGN PATENT DOCUMENTS

WO    1998039061 A2    9/1998

OTHER PUBLICATIONS

EPO Search report dated Sep. 27, 2018 on EP Application 18186229.3-1224.

(Continued)

*Primary Examiner* — Erin M Piateski
(74) *Attorney, Agent, or Firm* — Spectrum IP Law Group LLC

(57) ABSTRACT

In embodiments a WCD system is worn and/or carried by an ambulatory patient. The WCD system analyzes an ECG signal of the patient, to determine whether or not the patient should be given an electric shock to restart their heart. If so, then the WCD system first gives a preliminary alarm to the patient, asking them to prove they are alive if they are. The WCD system further determines whether the ECG signal contains too much High Amplitude (H-A) noise, which can distort the analysis of the ECG signal. If too much H-A noise is detected for a long time, the WCD system may eventually alert the patient about their activity, so that the ECG noise may be abated. The WCD system may even pause the analysis of the ECG signal, so that there will be no preliminary alarms that could be false until the ECG noise is abated.

27 Claims, 9 Drawing Sheets

STATE OF NOISE-DETECTED FLAG DEPENDING ON NOISE EVENTS DETECTED IN ECG

(51) Int. Cl.
    *A61B 5/0456*    (2006.01)
    *A61B 5/00*      (2006.01)
(52) U.S. Cl.
    CPC ....... *A61N 1/39046* (2017.08); *A61N 1/3975* (2013.01); *A61N 1/3993* (2013.01); *A61B 5/0456* (2013.01); *A61B 5/7203* (2013.01)
(58) Field of Classification Search
    CPC .... A61N 1/3993; A61B 5/0456; A61B 5/7203
    USPC .......................................................... 607/7
    See application file for complete search history.

(56) References Cited

U.S. PATENT DOCUMENTS

| | | | |
|---|---|---|---|
| 4,617,938 A * | 10/1986 | Shimoni | A61B 5/0452 600/521 |
| 4,619,265 A | 10/1986 | Morgan et al. | |
| 4,928,690 A | 5/1990 | Heilman et al. | |
| 4,955,381 A | 9/1990 | Way et al. | |
| 5,078,134 A | 1/1992 | Heilman et al. | |
| 5,228,449 A | 7/1993 | Christ et al. | |
| 5,348,008 A | 9/1994 | Bomn et al. | |
| 5,353,793 A | 10/1994 | Bornn | |
| RE34,800 E | 11/1994 | Hutchins | |
| 5,394,892 A | 3/1995 | Kenny | |
| 5,405,362 A | 4/1995 | Kramer et al. | |
| 5,474,574 A | 12/1995 | Payne et al. | |
| 5,662,690 A | 9/1997 | Cole et al. | |
| 5,709,215 A | 1/1998 | Perttu et al. | |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 5,944,669 A | 8/1999 | Kaib | |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder | |
| 6,427,083 B1 | 7/2002 | Owen et al. | |
| 6,437,083 B1 | 7/2002 | Owen et al. | |
| 6,529,875 B1 | 3/2003 | Nakajima | |
| 6,546,285 B1 | 4/2003 | Owen et al. | |
| 6,671,545 B2 | 12/2003 | Fincke | |
| 6,681,003 B2 | 1/2004 | Linder et al. | |
| 6,762,917 B1 | 7/2004 | Verbiest et al. | |
| 7,065,401 B2 | 6/2006 | Worden | |
| 7,559,902 B2 | 7/2009 | Ting et al. | |
| 7,865,238 B2 | 1/2011 | Brink | |
| 7,870,761 B2 | 1/2011 | Valentine et al. | |
| 7,974,689 B2 | 7/2011 | Volpe et al. | |
| 8,135,462 B2 | 3/2012 | Owen et al. | |
| 8,140,154 B2 | 10/2012 | Donnelly et al. | |
| 8,369,944 B2 | 2/2013 | Macho et al. | |
| 8,548,557 B2 | 10/2013 | Garstka et al. | |
| 8,615,295 B2 | 12/2013 | Savage et al. | |
| 8,644,925 B2 | 2/2014 | Volpe et al. | |
| 8,838,235 B2 | 9/2014 | Cowan et al. | |
| 8,897,860 B2 | 11/2014 | Volpe et al. | |
| 8,904,214 B2 | 12/2014 | Volpe et al. | |
| 8,965,500 B2 | 2/2015 | Macho et al. | |
| 9,008,801 B2 | 4/2015 | Kaib et al. | |
| 9,089,685 B2 | 7/2015 | Sullivan et al. | |
| 9,131,901 B2 | 9/2015 | Volpe et al. | |
| 9,132,267 B2 | 9/2015 | Kaib | |
| 9,408,548 B2 | 8/2016 | Volpe et al. | |
| 9,454,219 B2 | 9/2016 | Volpe et al. | |
| 9,533,165 B1 | 1/2017 | Gunderson | |
| 9,592,403 B2 | 3/2017 | Sullivan | |
| 2003/0158593 A1 | 8/2003 | Heilman et al. | |
| 2005/0107833 A1 | 5/2005 | Freeman et al. | |
| 2005/0107834 A1 | 5/2005 | Freeman et al. | |
| 2008/0312709 A1 | 12/2008 | Volpe et al. | |
| 2009/0005827 A1 | 1/2009 | Weintraub et al. | |
| 2010/0007413 A1 | 1/2010 | Herleikson | |
| 2010/0298899 A1 | 11/2010 | Donnelly et al. | |
| 2011/0022105 A9 | 1/2011 | Owen et al. | |
| 2011/0288604 A1 | 11/2011 | Kaib et al. | |
| 2011/0288605 A1 | 11/2011 | Kaib et al. | |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0265265 A1 | 10/2012 | Razavi et al. | |
| 2012/0283794 A1 | 11/2012 | Kaib et al. | |
| 2012/0293323 A1 | 11/2012 | Kaib et al. | |
| 2012/0302860 A1 | 11/2012 | Volpe et al. | |
| 2012/0310315 A1 | 12/2012 | Savage et al. | |
| 2013/0085538 A1 | 4/2013 | Volpe et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0317852 A1 | 11/2013 | Worrell et al. | |
| 2013/0325078 A1 | 12/2013 | Whiting et al. | |
| 2014/0025131 A1 | 1/2014 | Sullivan et al. | |
| 2014/0070957 A1 | 3/2014 | Longinotti-Buitoni et al. | |
| 2014/0163663 A1 | 6/2014 | Poddar et al. | |
| 2014/0324112 A1 | 10/2014 | Macho et al. | |
| 2014/0378812 A1 | 12/2014 | Saroka et al. | |
| 2015/0039053 A1 | 2/2015 | Kaib et al. | |
| 2015/0328472 A1* | 11/2015 | Sullivan | A61N 1/046 607/7 |
| 2016/0000349 A1* | 1/2016 | Sullivan | A61B 5/6802 600/509 |
| 2016/0004831 A1 | 1/2016 | Carlson et al. | |
| 2016/0082277 A1 | 3/2016 | Foshee, Jr. et al. | |
| 2018/0028083 A1* | 2/2018 | Greenhut | A61B 5/02405 |
| 2018/0116537 A1 | 5/2018 | Sullivan et al. | |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

Pagan-Carlo, et al., "Encircling Overlapping Multipulse Shock Waveforms for Transthoracic Defibrillation," JACC Journals, Dec. 1998, vol. 32 Issue 7, pp. 2065-2071.

* cited by examiner

SAMPLE COMPONENTS OF WEARABLE CARDIOVERTER DEFIBRILLATOR (WCD) SYSTEM

SAMPLE COMPONENTS OF EXTERNAL DEFIBRILLATOR

FIG. 4  METHODS

DETECTION OF H-A NOISE EVENT BY CRITERION OF TOO-LARGE R PEAK AMPLITUDE

WEARABLE CARDIOVERTER DEFIBRILLATOR (WCD) SYSTEM REACTING TO HIGH-AMPLITUDE ECG NOISE

CROSS REFERENCE TO RELATED PATENT APPLICATIONS

This patent application claims priority from U.S. Provisional Patent Application Ser. No. 62/538,145, filed on Jul. 28, 2017.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim.

Some people have an increased risk of SCA. People at a higher risk include patients who have had a heart attack, or a prior SCA episode. A frequent recommendation is for these people to receive an Implantable Cardioverter Defibrillator (ICD). The ICD is surgically implanted in the chest, and continuously monitors the patient's electrocardiogram (ECG). If certain types of heart arrhythmias are detected, then the ICD delivers an electric shock through the heart.

After being identified as having an increased risk of an SCA, and before receiving an ICD, these people are sometimes given a Wearable Cardioverter Defibrillator (WCD) system. (Early versions of such systems were called wearable cardiac defibrillator systems.) A WCD system typically includes a harness, vest, or other garment that the patient is to wear. The WCD system further includes electronic components, such as a defibrillator and electrodes, coupled to the harness, vest, or other garment. When the patient wears the WCD system, the external electrodes may then make good electrical contact with the patient's skin, and therefore can help sense the patient's ECG. If a shockable heart arrhythmia is detected, then the defibrillator delivers the appropriate electric shock through the patient's body, and thus through the heart.

Often the patient's ECG includes electrical noise, which can be created at the interface of the electrodes with the patient's skin. Such noise can make it difficult to diagnose the patient's condition accurately from the ECG, and detect whether or not the patient is having a shockable arrhythmia.

All subject matter discussed in this Background section of this document is not necessarily prior art, and may not be presumed to be prior art simply because it is presented in this Background section. Plus, any reference to any prior art in this description is not, and should not be taken as, an acknowledgement or any form of suggestion that such prior art forms parts of the common general knowledge in any art in any country. Along these lines, any recognition of problems in the prior art discussed in this Background section or associated with such subject matter should not be treated as prior art, unless expressly stated to be prior art. Rather, the discussion of any subject matter in this Background section should be treated as part of the approach taken towards the particular problem by the inventors. This approach in and of itself may also be inventive.

BRIEF SUMMARY

The present description gives instances of wearable cardioverter defibrillator (WCD) systems, storage media that may store programs, and methods, the use of which may help overcome problems and limitations of the prior art.

In embodiments a WCD system is worn and/or carried by an ambulatory patient. The WCD system analyzes an ECG signal of the patient, to determine whether or not the patient should be given an electric shock to restart their heart. If so, then the WCD system first gives a preliminary alarm to the patient, asking them to prove they are alive if they are. The WCD system further determines whether the ECG signal contains too much High Amplitude (H-A) noise, which can distort the analysis of the ECG signal. If too much H-A noise is detected for a long time, the WCD system may eventually alert the patient about their activity, so that the ECG noise may be abated. The WCD system may even pause the analysis of the ECG signal, so that there will be no preliminary alarms that could be false until the ECG noise is abated.

Another advantage can be that, with fewer false preliminary alarms, the patient can be more compliant in actually wearing and/or carrying the WCD system.

These and other features and advantages of the claimed invention will become more readily apparent in view of the embodiments described and illustrated in this specification, namely in this written specification and the associated drawings.

DETAILED DESCRIPTION

As has been mentioned, the present description is about wearable cardioverter defibrillator (WCD) systems, media that store instructions, and methods. Embodiments are now described in more detail.

A wearable cardioverter defibrillator (WCD) system made according to embodiments has a number of components. These components can be provided separately as modules that can be interconnected, or can be combined with other components, etc.

Figure 1:
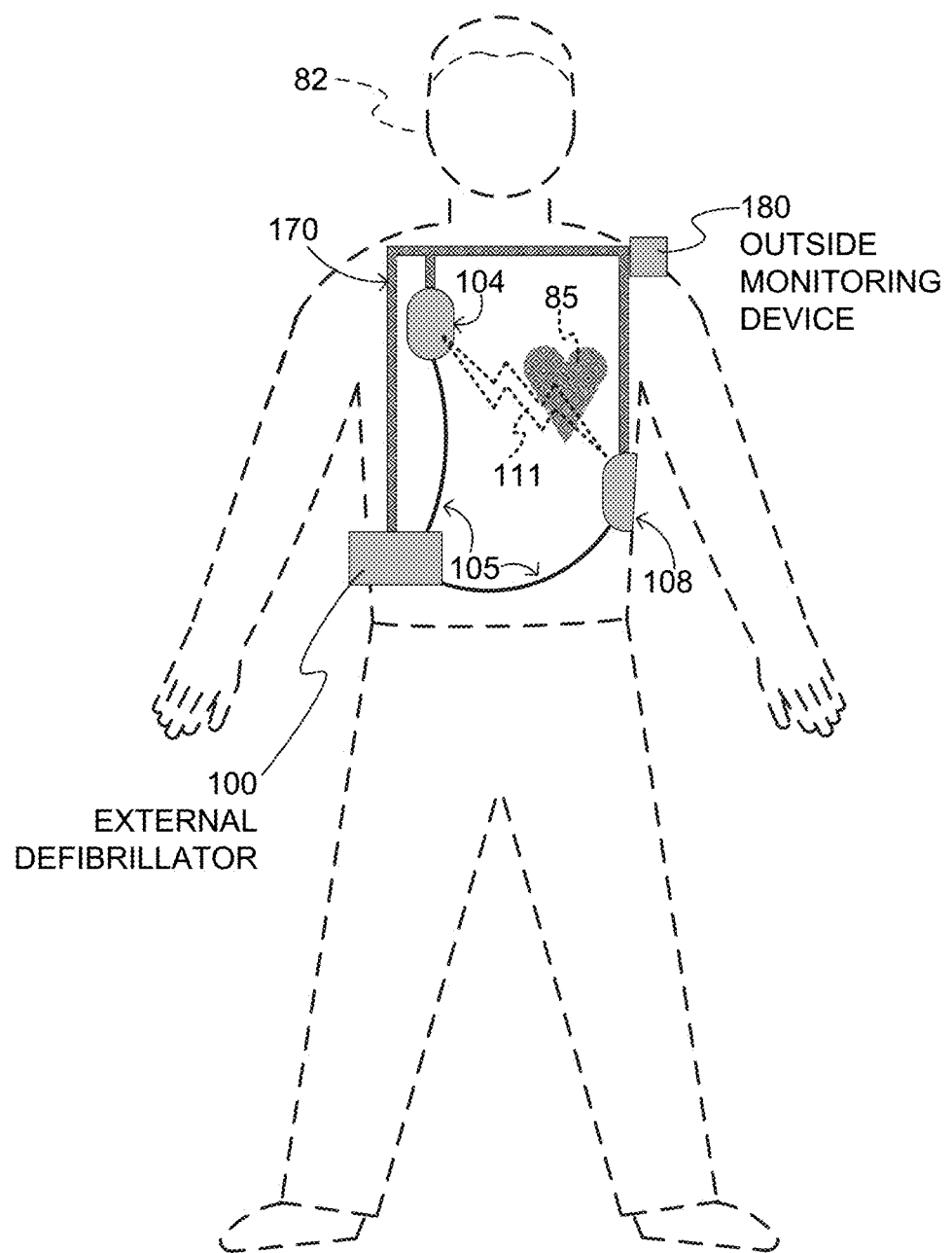
FIG. 1 is a diagram of components of a sample wearable cardioverter defibrillator (WCD) system, made according to embodiments.

FIG. 1 depicts a patient 82. Patient 82 may also be referred to as a person and/or wearer, since the patient is wearing components of the WCD system. Patient 82 is ambulatory, which means patient 82 can walk around, and is not necessarily bed-ridden.

FIG. 1 also depicts components of a WCD system made according to embodiments. One such component is a support structure 170 that is wearable by patient 82. It will be understood that support structure 170 is shown only generically in FIG. 1, and in fact partly conceptually. FIG. 1 is provided merely to illustrate concepts about support structure 170, and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to parallel articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient by adhesive material, for example as shown in U.S. Pat. No. 8,024,037. Support structure 170 can even be implemented as described for the support structure of US Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/0056682 document. There can be other examples.

A WCD system according to embodiments is configured to defibrillate a patient who is wearing it, by delivering an electrical charge to the patient's body in the form of an electric shock delivered in one or more pulses. FIG. 1 shows a sample external defibrillator 100, and sample defibrillation electrodes 104, 108, which are coupled to external defibrillator 100 via electrode leads 105. Defibrillator 100 and defibrillation electrodes 104, 108 can be coupled to support structure 170. As such, many of the components of defibrillator 100 could be therefore coupled to support structure 170. When defibrillation electrodes 104, 108 make good electrical contact with the body of patient 82, defibrillator 100 can administer, via electrodes 104, 108, a brief, strong electric pulse 111 through the body. Pulse 111 is also known as shock, defibrillation shock, therapy and therapy shock. Pulse 111 is intended to go through and restart heart 85, in an effort to save the life of patient 82. Pulse 111 can further include one or more pacing pulses, and so on.

A prior art defibrillator typically decides whether to defibrillate or not based on an ECG signal of the patient. However, external defibrillator 100 may initiate defibrillation (or hold-off defibrillation) based on a variety of inputs, with ECG merely being one of them.

Accordingly, it will be appreciated that signals such as physiological signals containing physiological data can be obtained from patient 82. While the patient may be considered also a "user" of the WCD system, this is not a requirement. That is, for example, a user of the wearable cardioverter defibrillator (WCD) may include a clinician such as a doctor, nurse, emergency medical technician (EMT) or other similarly situated individual (or group of individuals). The particular context of these and other related terms within this description should be interpreted accordingly.

The WCD system may optionally include an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document. Device 180 may include one or more transducers or sensors that are configured to render one or more physiological inputs or signals from one or more patient parameters that they sense.

Optionally, device 180 is physically coupled to support structure 170. In addition, device 180 can be communicatively coupled with other components, which are coupled to support structure 170. Such communication can be implemented by a communication module, as will be deemed applicable by a person skilled in the art in view of this description.

Figure 2:
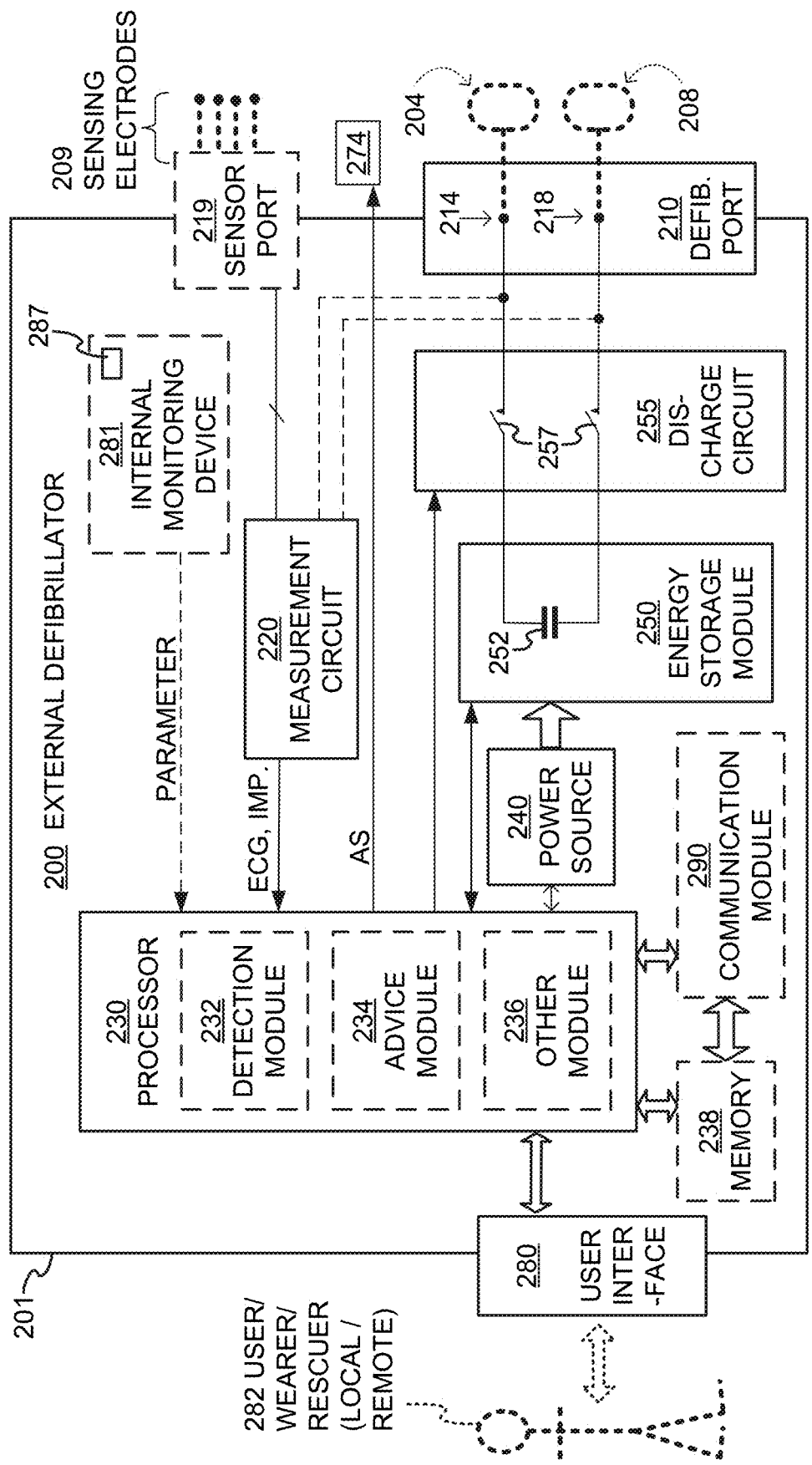
FIG. 2 is a diagram showing sample components of an external defibrillator, such as the one belonging in the system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as patient 82 of FIG. 1. Defibrillator 200 may further include a user interface 280 for a user 282. User 282 can be patient 82, also known as wearer 82. Or, user 282 can be a local rescuer at the scene, such as a bystander who might offer assistance, or a trained person. Or, user 282 might be a remotely located trained caregiver in communication with the WCD system.

User interface 280 can be made in a number of ways. User interface 280 may include output devices, which can be visual, audible or tactile, for communicating to a user by outputting images, sounds or vibrations. Images, sounds, vibrations, and anything that can be perceived by user 282 can also be called human-perceptible indications. There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds and/or words to warn bystanders, etc.

User interface 280 may further include input devices for receiving inputs from users. Such input devices may additionally include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which of monitoring devices 180, 281 can be done according to design considerations. Device 281 may include one or more transducers or sensors that are configured to render one or more physiological inputs from one or more patient parameters that it senses.

Patient parameters may include patient physiological parameters. Patient physiological parameters may include, for example and without limitation, those physiological parameters that can be of any help in detecting by the wearable defibrillation system whether the patient is in need of a shock, plus optionally their medical history and/or event history. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an $SpO_2$ sensor, and so on. In view of this disclosure, it will be appreciated that such sensors can help detect the patient's pulse, and can therefore also be called pulse detection sensors, pulse sensors, and pulse rate sensors. Pulse detection is also taught at least in Physio-Control's U.S. Pat. No. 8,135,462, which is hereby incorporated by reference in its entirety. In addition, a person skilled in the art may implement other ways of performing pulse detection. In such cases, the transducer includes an appropriate sensor, and the physiological input is a measurement by the sensor of that patient parameter. For example, the appropriate sensor for a heart sound may include a microphone, etc.

In some embodiments, the local parameter is a trend that can be detected in a monitored physiological parameter of patient 282. A trend can be detected by comparing values of parameters at different times. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$ or $CO_2$; f) respiratory function, respiratory rate, etc.; g) motion, level of activity; and so on. Once a trend is detected, it can be stored and/or reported via a communication link, along perhaps with a warning. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may include a motion detector. In embodiments, a motion detector can be implemented within monitoring device 180 or monitoring device 281. Such a motion detector can be made in many ways as is known in the art, for example by using an accelerometer. In this example, a motion detector 287 is implemented within monitoring device 281.

A motion detector of a WCD system according to embodiments can be configured to detect a motion event. In response, the motion detector may render or generate, from the detected motion event or motion, a motion detection input that can be received by a subsequent device or functionality. A motion event can be defined as is convenient, for example a change in motion from a baseline motion or rest, etc. In such cases, a sensed patient parameter is motion.

System parameters of a WCD system can include system identification, battery status, system date and time, reports of self-testing, records of data entered, records of episodes and intervention, and so on.

Environmental parameters can include ambient temperature and pressure. Moreover, a humidity sensor may provide information as to whether it is likely raining. Presumed patient location could also be considered an environmental parameter. The patient location could be presumed, if monitoring device 180 or 281 includes a GPS location sensor as per the above, and if it is presumed that the patient is wearing the WCD system.

Defibrillator 200 typically includes a defibrillation port 210, such as a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer the electrical charge that has been stored in an energy storage module 250 that is described more fully later in this document. The electric charge will be the shock for defibrillation, pacing, and so on.

Defibrillator 200 may optionally also have a sensor port 219 in housing 201, which is also sometimes known as an ECG port. Sensor port 219 can be adapted for plugging in sensing electrodes 209, which are also known as ECG electrodes and ECG leads. It is also possible that sensing electrodes 209 can be connected continuously to sensor port 219, instead. Sensing electrodes 209 are types of transducers that can help sense an ECG signal, e.g. a 12-lead signal, or a signal from a different number of leads, especially if they make good electrical contact with the body of the patient and in particular with the skin of the patient. Sensing electrodes 209 can be attached to the inside of support structure 170 for making good electrical contact with the patient, similarly with defibrillation electrodes 204, 208.

Optionally a WCD system according to embodiments also includes a fluid that it can deploy automatically between the electrodes and the patient's skin. The fluid can be conductive, such as by including an electrolyte, for establishing a better electrical contact between the electrode and the skin. Electrically speaking, when the fluid is deployed, the electrical impedance between the electrode and the skin is reduced. Mechanically speaking, the fluid may be in the form of a low-viscosity gel, so that it does not flow away from the electrode, after it has been deployed. The fluid can be used for both defibrillation electrodes 204, 208, and for sensing electrodes 209.

The fluid may be initially stored in a fluid reservoir, not shown in FIG. 2, which can be coupled to the support structure. In addition, a WCD system according to embodiments further includes a fluid deploying mechanism 274. Fluid deploying mechanism 274 can be configured to cause at least some of the fluid to be released from the reservoir, and be deployed near one or both of the patient locations, to which the electrodes are configured to be attached to the patient. In some embodiments, fluid deploying mechanism 274 is activated prior to the electrical discharge responsive to receiving activation signal AS from a processor 230, which is described more fully later in this document.

The intent for a WCD system is to shock when needed, and not shock when not needed. An ECG signal may provide sufficient data for making a shock/no shock determination. The problem is that, at any given point in time, some of these ECG signals may include noise, while others not. The noise may be due to patient movement, how well the electrodes contact the skin, and so on. The inventor has identified that some types of ECG noise for a WCD system can be classified as High-Frequency (H-F) noise, while other types of such ECG noise can be classified as High-Amplitude (H-A) noise. The noise problem for a WCD may be further exacerbated by the desire to use dry, non-adhesive monitoring electrodes. Dry, non-adhesive electrodes are thought to be more comfortable for the patient to wear in the long term, but may produce more noise than a conventional ECG monitoring electrode that includes adhesive to hold the electrode in place and an electrolyte gel to reduce the impedance of the electrode-skin interface.

Defibrillator 200 also includes a measurement circuit 220, as one or more of its sensors or transducers. Measurement circuit 220 senses one or more electrical physiological signals of the patient from sensor port 219, if provided. Even if defibrillator 200 lacks sensor port 219, measurement circuit 220 may optionally obtain physiological signals through nodes 214, 218 instead, when defibrillation electrodes 204, 208 are attached to the patient. In these cases, the physiological input reflects an ECG measurement. The patient parameter can be an ECG, which can be sensed as a voltage difference between electrodes 204, 208. In addition the patient parameter can be an impedance, which can be sensed between electrodes 204, 208 and/or the connections of sensor port 219. Sensing the impedance can be useful for detecting, among other things, whether these electrodes 204, 208 and/or sensing electrodes 209 are not making good electrical contact with the patient's body. These patient physiological signals can be sensed, when available. Measurement circuit 220 can then render or generate information about them as physiological inputs, data, other signals, etc. More strictly speaking, the information rendered by measurement circuit 220 is output from it, but this information can be called an input because it is received by a subsequent device or functionality as an input.

Defibrillator 200 also includes a processor 230. Processor 230 may be implemented in a number of ways. Such ways include, by way of example and not of limitation, digital and/or analog processors such as microprocessors and Digital Signal Processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also referred to as "software," generally provide functionality by performing methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document. Processor 230 may, among other functions, set a flag, unset a flag, and so on.

Processor 230 can be considered to have a number of modules. One such module can be a detection module 232. Detection module 232 can include a Ventricular Fibrillation (VF) detector. The patient's sensed ECG from measurement circuit 220, which can be available as physiological inputs, data, or other signals, may be used by the VF detector to determine whether the patient is experiencing VF. Detecting VF is useful, because VF typically results in SCA. Detection module 232 can also include a Ventricular Tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments, and determining whether a shock criterion is met. The determination can be made from a rhythm analysis of the captured ECG signal or otherwise.

In some embodiments, when the determination is to shock, an electrical charge is delivered to the patient. Delivering the electrical charge is also known as discharging. Shocking can be for defibrillation, pacing, and so on.

Processor 230 can include additional modules, such as other module 236, for other functions. In addition, if internal monitoring device 281 is indeed provided, it may be operated in part by processor 230, etc.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in functions, operations, processes, actions and/or methods to be performed, and/or the processor to cause other devices or components or blocks to perform such functions, operations, processes, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or stored there after it is received by defibrillator 200.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy-storing capacitor, and so on. In some embodiments, power source 240 is controlled by processor 230. Appropriate components may be included to provide for charging or replacing power source 240.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

Defibrillator 200 moreover includes a discharge circuit 255. When the decision is to shock, processor 230 can be configured to control discharge circuit 255 to discharge through the patient the electrical charge stored in energy storage module 250. When so controlled, circuit 255 can permit the energy stored in module 250 to be discharged to nodes 214, 218, and from there also to defibrillation electrodes 204, 208, so as to cause a shock to be delivered to the patient. Circuit 255 can include one or more switches 257. Switches 257 can be made in a number of ways, such as by an H-bridge, and so on. Circuit 255 can also be controlled via user interface 280.

Defibrillator 200 can optionally include a communication module 290, for establishing one or more wired or wireless communication links with other devices of other entities, such as a remote assistance center, Emergency Medical Services (EMS), and so on. The data can include patient data, event information, therapy attempted, CPR performance, system data, environmental data, and so on. For example, communication module 290 may transmit wirelessly, e.g. on a daily basis, heart rate, respiratory rate, and other vital signs data to a server accessible over the internet, for instance as described in US 20140043149. This data can be analyzed directly by the patient's physician and can also be analyzed automatically by algorithms designed to detect a developing illness and then notify medical personnel via text, email, phone, etc. Module 290 may also include such interconnected sub-components as may be deemed necessary by a person skilled in the art, for example an antenna, portions of a processor, supporting electronics, outlet for a telephone or a network cable, etc. This way, data, commands, etc. can be communicated.

Defibrillator 200 can optionally include other components.

Figure 3:
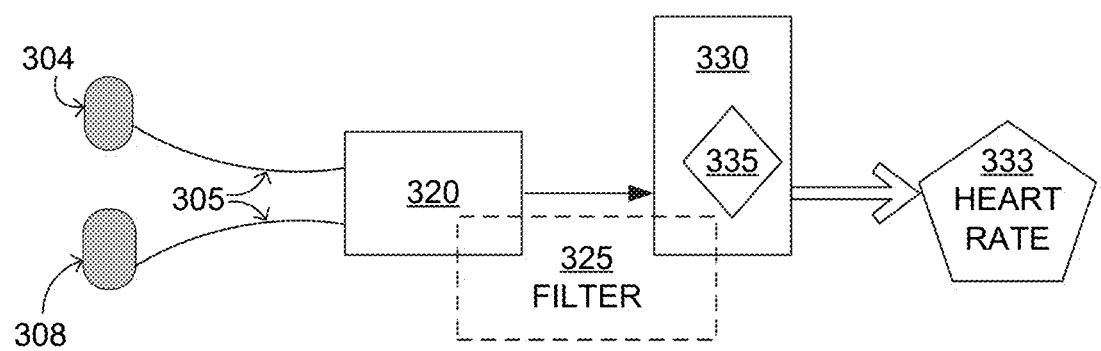
FIG. 3 is a diagram of selected components for illustrating how an ECG signal sensed by a pair of electrodes may be processed according to embodiments to yield a heart rate and other information.

Operations according to embodiments is now described in more detail. FIG. 3 is a conceptual diagram for illustrating how electrodes of a WCD system may sense or capture ECG signals of the patient, and how these sensed ECG signals may be used according to embodiments to yield a heart rate of the patient and other information. Two electrodes 304, 308 are attached to the torso of a patient, who is not shown. It will be appreciated that electrical noise may be introduced into the ECG signal at this point. Each of electrodes 304, 308 has a wire lead 305. Together, electrodes 304, 308 sense an ECG signal of the patient along a single vector. Additional ECG signals may be sensed along additional vectors.

FIG. 3 also shows a measurement circuit 320 and a processor 330, which can be made as described for measurement circuit 220 and processor 230. A filter 325 is optionally implemented in measurement circuit 320 and/or in processor 330. Filter 325 may be implemented as an analog filter, a digital filter, and so on. Filter 325 may help overcome some types of ECG noise by suppressing it, making this noise easier to detect, and so on.

Processor 330 may perform a full ECG rhythm analysis 335. As a result of such an analysis 335, a shock/no shock decision may be arrived at, and so on. Sometimes as a precursor to analysis 335, processor 330 may compute a heart rate 333 according to embodiments. A computation of heart rate 333 maybe repeated, if the result of a previous computation does not meet a confidence criterion. The computation of heart rate 333 may be thus repeated in the same way, or in a different way, for example with additional safeguards, such as for addressing noise in the ECG signal. Plus, for a full ECG rhythm analysis 335 additional more parameters may be computed, such as a QRS width and so on.

Computed heart rate 333 and the results of analysis 335 may be further used in additional ways. For example, they may be stored in memory 238, downloaded later from memory 238, transmitted wirelessly via communication module 290, displayed by a screen of user interface 280, and so on.

The devices and/or systems mentioned in this document perform functions, processes and/or methods. These functions, processes and/or methods may be implemented by one or more devices that include logic circuitry. Such a device can be alternately called a computer, and so on. It may be a standalone device or computer, such as a general purpose computer, or part of a device that has one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description includes flowcharts, display images, algorithms, and symbolic representations of program operations within at least one computer readable medium. An economy is achieved in that a single set of flowcharts is used to describe both programs, and also methods. So, while flowcharts described methods in terms of boxes, they also concurrently describe programs.

Methods are now described.

Figure 4:
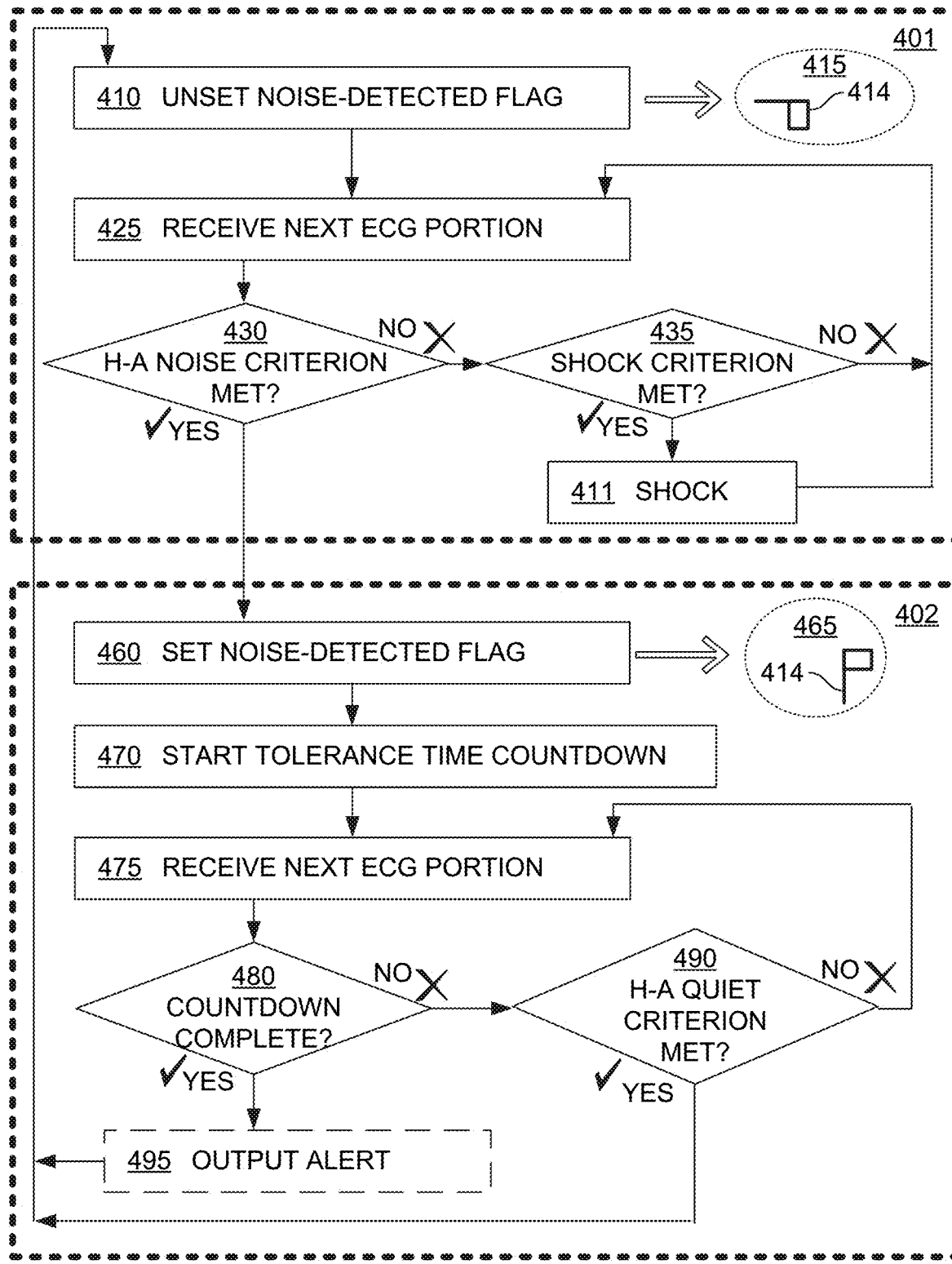
FIG. 4 is a flowchart for illustrating sample methods according to embodiments.

FIG. 4 shows a flowchart 400 for describing methods according to embodiments. The operations of flowchart 400 can be broadly divided in a first group 401 and in a second group 402. First group 401 is distinguished from second group 402 according to the current state of a flag 414, which is also called a noise-detected flag 414. According to a comment oval 415, for operations in first group 401 flag 414 is unset, and is shown as lowered. According to a comment oval 465, for operations in second group 402 flag 414 is set, and is shown as raised.

A current value of flag 414, namely its current state of being set or unset, can be a value of a parameter maintained in software, or expressed by a state machine of processor 230 and/or related components, and so on. It will be appreciated that the current value of flag 414 can alternate between being set and being unset, as the execution of operations of flowchart 400 alternates between group 401 and 402.

Individual operations of flowchart 400 are now described.

A WCD system may start its operations from an operation 410. According to operation 410, noise-detected flag 414 can be unset, resulting in the orientation of comment oval 415. Flag 414 may be unset for a number of reasons, for example responsive to the sensed ECG signal meeting a High-Amplitude (H-A) quiet criterion, as will be seen later from operation 490. Or, flag 414 may be unset after a tolerance time passes since flag 414 was set, e.g. as per operation 480. Suitable such tolerance times can be 0.5 minutes (min), 1 min, 5, min, 10 min, 20 min, etc., as will be seen later from the description of operations 470 and 480. Or, flag 414 may be unset responsive to outputting an alert for patient 82, as will be seen later from operation 490.

According to another operation 425, a next ECG portion may be received where processing is taking place, such as in processor 230. Sample ECG portions 519 are shown in FIG. 5.

Figure 5:
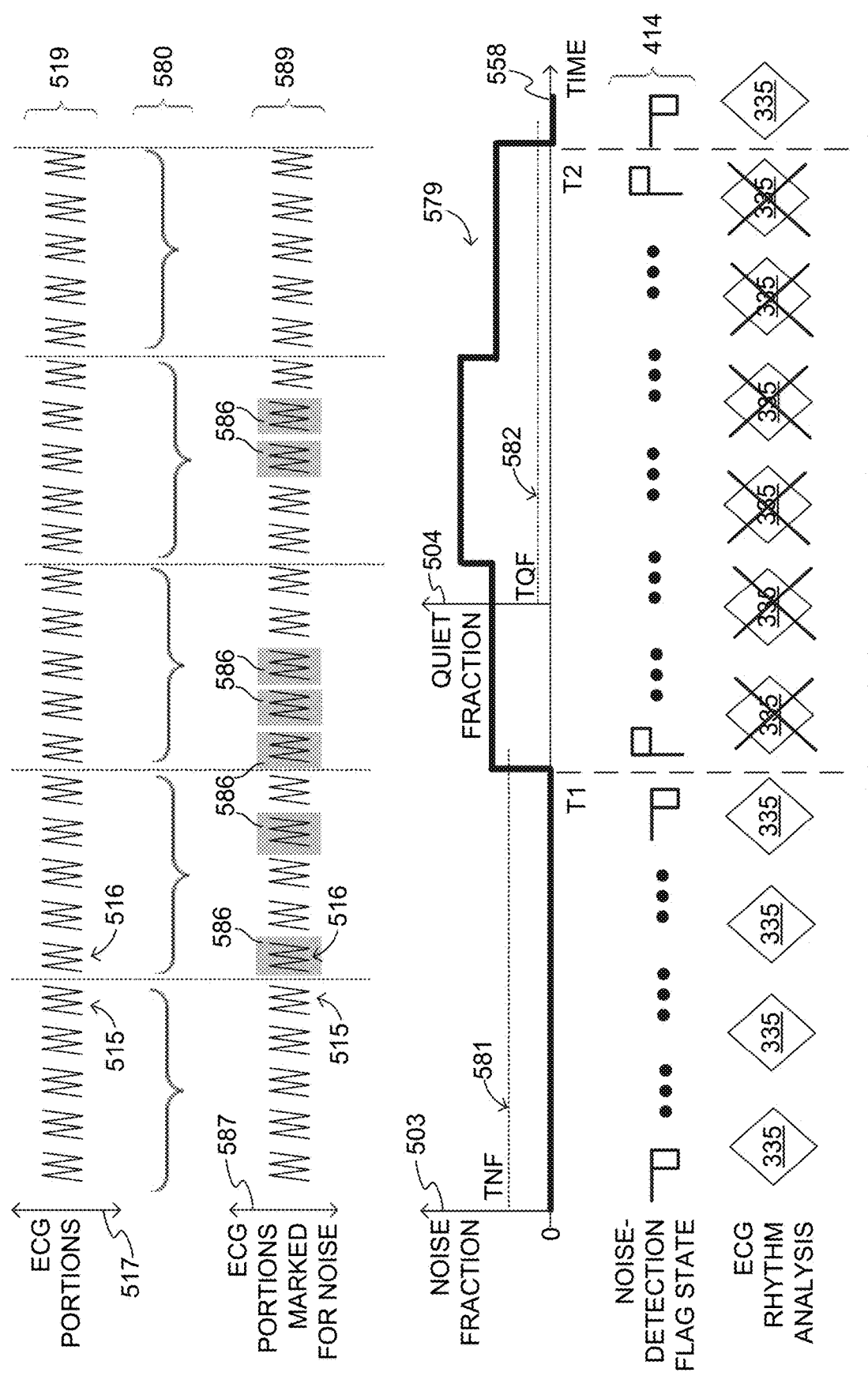
FIG. 5 is a diagram of a sample time sequence of ECG portions, sample groupings of these ECG portions, the same ECG portions after some of them have been marked about their noise, a resulting sample evolution of a noise fraction/quiet fraction, a resulting sample evolution of the states of a noise-detection flag, and a resulting sample evolution of when ECG rhythm analysis can pause being performed according to embodiments.

FIG. 5 shows sample time evolutions of a number of quantities according to embodiments, against a time axis 558. Sample ECG portions 519 are shown with reference to an ECG portions axis 517. Of those, two sample ECG portions 515, 516 are identified for subsequent explanations. In particular, starting from the ECG signal that can be sensed by the electrodes continuously, ECG portions of the sensed ECG signal can be defined. Such ECG portions can be defined in a number of ways. For example, each ECG portion can be a part of the sensed ECG signal that processor 230 processes at one time. An ECG portion may be long enough to perform a full ECG rhythm analysis 335. As such, An ECG portion may include several QRS complexes. Or an ECG portion may be shorter. In fact, in some embodiments, an ECG portion can be simply a peak identified in the ECG signal, which may be an R peak of a QRS complex. ECG portions can be stored in memory 238 for later analysis, repeated analysis, different analysis, and so on.

Each of ECG portions 519 is intended to be drawn generically in FIG. 5, while in fact they could have waveforms different from what is shown in FIG. 5. More particular examples will be shown later in this document. It will be recognized that, in the instances where an ECG signal actually has the exact appearance seen in FIG. 5, that ECG signal might indicate VT, or even VF, but that need not be the case for FIG. 5. In addition, ECG portions 519 are drawn contracted in FIG. 5, while some more expanded versions appear in FIG. 6.

Returning to FIG. 4, according to another operation 430, it can be determined whether or not the sensed ECG signal meets a High-Amplitude (H-A) noise criterion. This may be performed in a number of ways. In some embodiments, the H-A noise criterion is met responsive to a group of the most recent ECG portions 519 meeting a noise condition. Such a group can have any suitable number of ECG portions 519, for example from one to 10 ECG portions 519 per group. A good number is for a group to have 5 ECG portions 519. Sample such groupings 580 of ECG portions 519 are shown in FIG. 5.

Returning again to FIG. 4 if, at operation 430 the answer is NO, then according to another operation 435, it may be determined whether or not a shock criterion is met. The determination may be made from the sensed ECG signal, for example as was described for operation 335. Plus, as described later in more detail, in some embodiments the H-A noise criterion of operation 430 may be met by analyzing ECG segments for whether or not they meet a noise condition. In such embodiments, if the H-A noise criterion is not met, it can be determined whether or not the shock criterion is met for operation 435 only from the ECG portions that do not meet the noise condition.

If at operation 435 the answer is NO, the execution may return to an earlier operation, such as operation 425. For as long as the H-A noise criterion of operation 430 is not being met and the patient is well, execution could continue to loop through operations 425, 430, 435 indefinitely.

If at operation 435 the answer is YES then, according to a shock operation 411, a shock 111 may be administered to patient 82. For shock operation 411, processor 230 may control, responsive to the shock criterion being met and noise-detected flag 414 being unset, discharge circuit 255 to discharge through patient 82 an electrical charge that is stored in energy storage module 250, while support structure 170 is worn by patient 82 so as to deliver a shock 111 to patient 82. Of course, before shock operation 411 is performed, another process may be undertaken where the patient is alerted by a preliminary alarm, challenged to demonstrate they are alive, and so on.

If at operation 430 the answer is YES, then according to another operation 460, noise-detected flag 414 may be set. In embodiments, therefore, noise-detected flag becomes set responsive to the sensed ECG signal meeting the H-A noise criterion at operation 430.

The reader will observe that, starting with operation 460, execution has now transitioned from first group of operations 401 to second group of operations 402. According to a comment oval 465, flag 414 is shown as set. While flag 414 is set, a number of aspects may be different.

First, in some embodiments the discharge circuit is controlled to not thus discharge when noise-detected flag 414 is set as per comment oval 465. This can be true even if it were thus determined that the shock criterion is met by another operation that is not shown in FIG. 4. In the example of FIG.

4, a shock operation similar to shock operation 411 is not among the second group of operations 402. And, as described above, this shock operation 411 first gives preliminary alarms to the patient, and so on. So, in these embodiments where the discharge circuit is controlled to not thus discharge when noise-detected flag 414 is set, patient 82 does not receive such preliminary alarms.

Second, in some embodiments it is not even determined whether or not the shock criterion is met when the noise-detected flag is set. In the example of FIG. 4, an operation similar to operation 435 is not among the second group of operations 402. As such, the patient's ECG might not be monitored while flag 414 is set. (At the same time, however, the patient may continue to be monitored by a monitoring device, a motion sensor whose signal might suggest that the patient is engaged in a certain activity, and so on.) But then again, the ECG that is not monitored may include too much high-amplitude noise, detected at operation 430, to give reliable answers. Indeed, high-amplitude noise tends to obscure the ECG signal. Rhythm analysis 335 during high-amplitude noise may generate results that are unpredictable, because they depend more on the noise than on the ECG signal.

While it is desirable to alert patient 82 that they should stop the activity that gives rise to the noise in the ECG signal, it is not a good idea to alert patient 82 too quickly, so as not to bother patient 82 unnecessarily. In any event, given enough time, high-amplitude noise often becomes abated without the intervention of alerting the patient.

Of course, if large amplitude noise persists for an extended period of time, the patient must be alerted to correct the situation. Sometimes the noise might be the result of activity on the part of the patient, and sometimes it might be due to a problem with the garment, such as a poor fit or electrodes that are too dry. So, tolerance time for purposes of this document is the time that a WCD system according to embodiments would tolerate neither analyzing the patient, nor alerting them. After that time passes, the WCD system may alert the patient and/or unset flag 414. Some tolerance times were indicated earlier in this document, and these can even be adjusted by what is suggested by other sensors such as a motion sensor.

For implementing a tolerance time, according to another, optional operation 470, a tolerance time countdown may be started. This may be by a clock or timer that counts up or down, and so on.

According to another operation 475, the next ECG portion may be received, similarly to what was described for operation 425. According to another, optional operation 480, it can be determined whether or not the countdown of operation 480 is complete.

If at operation 480 the answer is NO, then according to another, optional operation 490 it can be determined whether or not the H-A quiet criterion is met, for deciding that the noise in the ECG signal has been abated. This can be accomplished in a number of ways.

First, the H-A quiet criterion may be met responsive to the H-A noise criterion no longer being met. For example, another group of the most recent ECG portions may be considered, which are received later. For instance, at least one ECG portion of the other group may occur after at least one ECG portion of the group that was used to determine that the H-A noise criterion was being met in the first place. And the H-A quiet criterion may be thus met responsive to this other group of the most recent ECG portions not meeting the H-A noise condition.

Second, the H-A quiet criterion may be met responsive to different conditions than the H-A noise criterion. For instance, the H-A quiet criterion may be met responsive to the other, later group of the most recent ECG portions meeting a quiet condition, which is not the same as or an inverse of the noise condition.

Moreover, everything else described for determining whether or not the H-A noise criterion is met can be used analogously for determining whether or not the H-A quiet criterion is met. This includes what is described below for noisiness criteria, spuriousness criteria, and so on.

If at operation 490 the answer is NO, then execution may return to another operation from group 402, such as operation 475. If at operation 490 the answer is YES, however, then execution may return to operation 410, unsetting noise-detecting flag 414, and so on.

If at operation 480 the answer is NO, then according to another, optional operation 495, an alert can be output for the patient. As such, user interface 280 can be configured to output an alert, responsive to noise-detected flag 414 being set. The alert can be about correcting a noise situation. The alert can be output further responsive to the noise-detected flag having been set for the tolerance time. And, different tolerance times may be used for alerting and for exiting group 402. For example, group 402 may be exited more times than one before alerting per operation 495, and so on. After operation 495, execution may return to operation 410, unsetting noise-detecting flag 414, and so on.

As mentioned above, algorithms of WCD system embodiments can make decisions about whether noise is detected or not, for example by deciding whether or not certain conditions and/or criteria are met. Two such criteria have already been mentioned, namely the High-Amplitude (H-A) noise criterion of operation 430 and the H-A quiet criterion of operation 490. There are more such criteria and conditions, as algorithms according to embodiments begin with examining portions of the sensed ECG signal, and continue with the more detailed examination of identifying peaks in these ECG portions, and trying to determine whether these peaks are R peaks of QRS complexes or spikes due to high amplitude noise, which is also known as large amplitude noise.

As already mentioned above, in some embodiments the H-A noise criterion of operation 430 is met responsive to a group of the most recent ECG portions meeting a noise condition. And the H-A quiet criterion of operation 490 is met responsive to another group of the most recent ECG portions no longer meeting the noise condition, or meeting a different quiet condition, and so on.

In some embodiments, ECG portions of the group become marked responsive to meeting a noisiness criterion, examples of which are given later in this document. Then a fraction can be computed. The fraction can be of a number of the marked ECG portions of the group over a total number of the ECG portions of the group. For meeting the H-A noise criterion of operation 430, the fraction can be a so-called noise fraction, and the noise condition can be met responsive to the noise fraction exceeding a threshold noise fraction. On the other hand, for meeting the H-A quiet criterion of operation 490, the fraction can be the noise fraction, or a so-called quiet fraction. In the latter case, the quiet condition can be met responsive to the quiet fraction being less than a threshold quiet fraction. Examples are now described.

Returning to FIG. 5, ECG portions 519 include two consecutive sample ECG portions 515, 516. Groupings 580 are suggested for groups of five ECG portions at a time, which is a good number for a group size. In some embodiments groupings can be fixed, for example as suggested by groupings 580. At any one time, five ECG portions are considered as a single group, then the next five as another group, and so on, without overlap among the groups. For instance, the earliest group is made from the left-most five ECG portions, including ECG portion 515 but not including ECG portion 516. In other embodiments groupings can be variable, for instance counting only the most recent five ECG portions at any one time with overlap among the groups. The remainder of FIG. 5, however, proceeds with groupings 580 because they are visually more easy to follow due to the lack of overlap. As such, in the example of FIG. 5, each ECG portion belongs in a single group.

In FIG. 5, below groupings 580, ECG portions 589 repeat ECG portions 519 next to a vertical axis 587. In addition, some of ECG portions 589 are shown marked with a shadow 586. For example ECG portion 516 is marked with a shadow 586, but ECG portion 515 is not. As mentioned above, such marking can be for those of ECG portions 589 that meet a noisiness criterion. An easy way to think about the marked ECG portions is that they are "noisy".

The above-mentioned fraction can now be described in more detail. A diagram 579 shows the time evolution of a sample fraction using two vertical abscissa axes: a noise fraction axis 503, and then another a quiet fraction axis 504 that follows axis 503. Such fractions can be conveniently defined to have a value between 0 and 1.

In diagram 579, each of groupings 580 gives rise to a different value for the noise fraction. Generally it will be observed that there are more ECG portions 589 near the middle of time axis 558, which are marked with a shadow 586 due to being noisy. When considered in groupings 580, these noisy ECG portions 589 result in the noise fraction having the higher values of 0.4, 0.6 during the subsequent grouping 580. Moreover, the noise fraction has the value of zero in the beginning and the end of time axis 558.

So, as mentioned above, the noise condition can be met responsive to the noise fraction exceeding a threshold noise fraction. It is desired to set the noise flag when, in a group of five ECG portions, two or more are marked. So, the threshold noise fraction can be set at a value between 0.2 and 0.4, for example at 0.3. The value of 0.3 for the threshold noise fraction is shown by a dotted line 581, and a time intercept TNF on axis 503.

It will be observed that the plot of noise fraction 579 intersects dotted line 581 at time T1. In fact, that is how time T1 is defined. As such, the H-A noise criterion of operation 430 is answered YES for the first time at time T1.

After time T1, the next criterion that matters is the H-A quiet criterion of operation 490. This is indicated in FIG. 5 by axis 504 for the quiet fraction. In the example of FIG. 5, the quiet fraction is computed in the same way as the noise fraction.

As further mentioned above, the quiet condition can be met responsive to the quiet fraction being less than a threshold quiet fraction. In some embodiments, the threshold quiet fraction can be set at less than the threshold noise fraction, to make sure that the noise has been abated. For example, the threshold quiet fraction can be set at 0.1. As such, the quiet condition can be met when, in a group of 5 consecutive ECG portions 589, no ECG portion is marked. That value for the threshold quiet fraction of 0.1 is shown by a dotted line 582, and a time intercept TQF on axis 504.

It will be observed that the plot of noise fraction 579 intersects dotted line 582 at time T2. In fact, that is how time T2 is defined. As such, the H-A quiet criterion of operation 490 is answered YES for the first time at time T2. Of course, if the groupings were variable, time T2 would have occurred one ECG portion earlier. It will be further appreciated that, at time T1, a countdown may have been started for the tolerance time, according to operation 470. In the example of FIG. 5, time T2 was reached before such a countdown was complete at operation 480.

Accordingly, diagram 579 has provided the answers of times T1 and T2. Returning to FIG. 4, at time T1 execution transitions from operations group 401 to operations group 402. And, at time T2 execution transitions from operations group 402 back to operations group 401. As such, per comment oval 465, flag 414 is set or raised between times T1 and T2. And, per comment oval 415, flag 414 is unset or lowered for all other times of time axis 558.

FIG. 5. also shows the state of flag 414 at various times. It will be observed that flag 414 is shown raised between times T1 and T2, and lowered for all other times of time axis 558.

Moreover, as mentioned above, in some embodiments operation 335 does not take place while flag 414 is set or raised. This is also depicted graphically in the example of FIG. 5. As such, between times T1 and T2 there can be no false preliminary alarms to the patient due to a false decision to shock.

Figure 6:
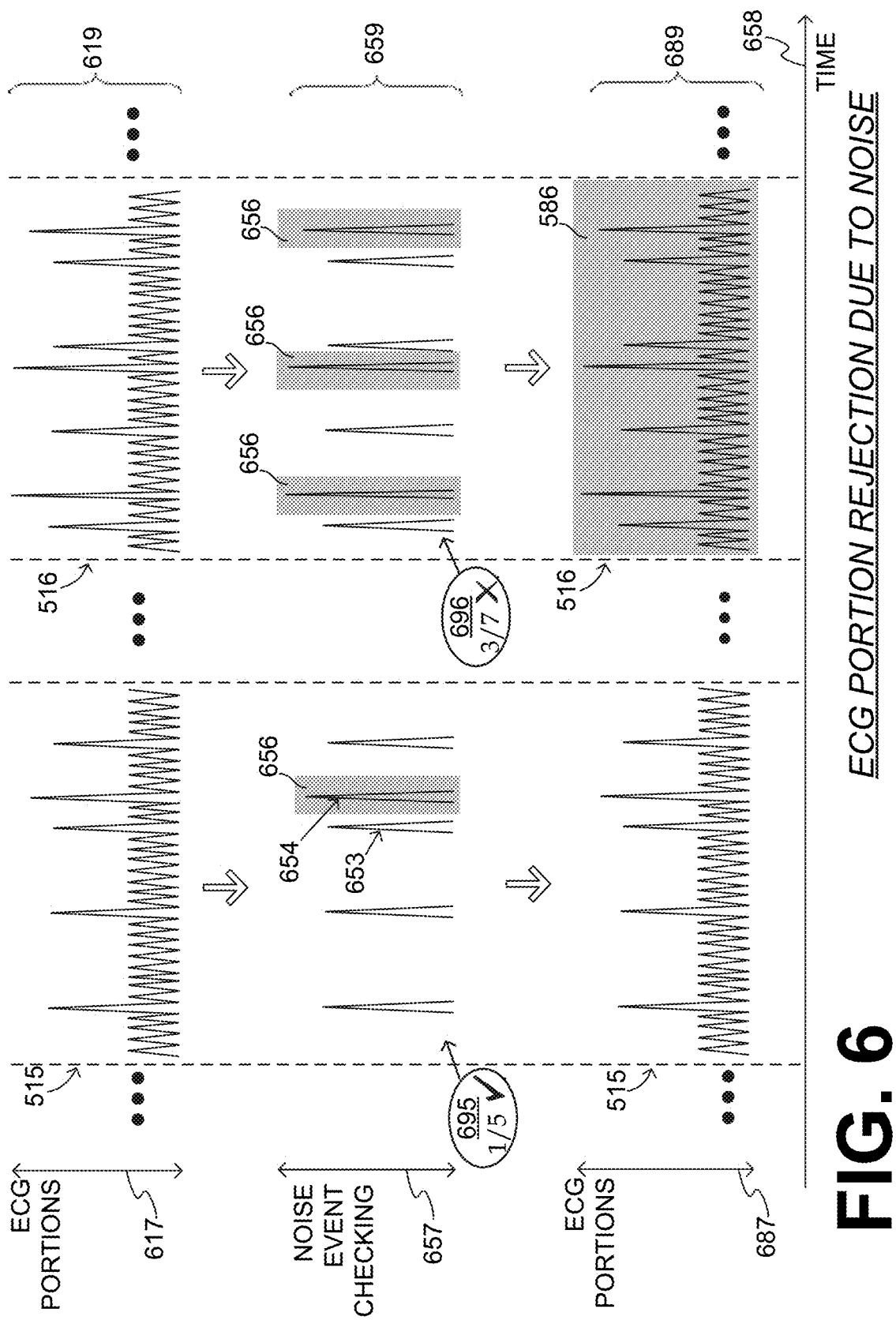
FIG. 6 shows time diagrams of sample ECG portions of FIG. 5, where decisions are made to mark when a noisiness criterion is met according to embodiments.

Examples are now described for how it can be decided which of ECG portions 589 to mark, which means deciding whether or not an ECG portion meets a noisiness criterion. FIG. 6 shows ECG portions 619, which repeat ECG portions 515, 516 of FIG. 5. In FIG. 6, ECG portions 515, 516 are shown more fully, but still somewhat idealized (for example the baseline level is not changing, etc.).

In some embodiments, potential R peaks 659 of QRS complexes are identified in a certain ECG portion, such as ECG portions 515, 516. As can be seen in FIG. 6, these potential R peaks 659 can be, for example, peaks with much higher amplitude than their neighbor peaks. Of those, two sample peaks are 653, 654.

Moreover, some of the identified potential R peaks 659 in ECG portions 515, 516 can be deemed invalid, if they meet a spuriousness criterion that is described later in this document. In the example of FIG. 6, the identified potential R peaks 659 that are deemed invalid are further shown each with a shadow 656. Potential R peak 653 is acceptable, does not meet the spuriousness criterion, and is not marked with a shadow. However, potential R peak 654 meet the spuriousness criterion, and therefore is deemed invalid and is marked with a shadow 656.

Then a validity ratio can be defined for ECG portions 515, 516. In each case the validity ratio can be a number of the potential R peaks in the ECG portion that are deemed invalid over a total number of the identified potential R peaks the ECG portion. As such, a validity ratio will have values between 0 and 1.

In such embodiments, the certain ECG portion may meet the noisiness criterion responsive to the validity ratio exceeding a threshold validity ratio. A good threshold validity ratio can be about 1/4. So, for practical purposes, the threshold validity ratio can be set at 0.24.

For example, per comment oval 695, for ECG portion 515 the validity ratio is 1/5=0.2, which is less than 0.24. As such, ECG portion 515 is acceptable, and it is not deemed invalid. Therefore, ECG portion 515 is repeated as ECG portion 689 without being marked by a shadow, similarly with FIG. 5.

For another example, per comment oval 696, for ECG portion 516 the validity ratio is 3/7=0.43, which is more than 0.24. As such, ECG portion 516 is not acceptable, and is deemed invalid. Therefore, ECG portion 516 is repeated as ECG portion 689 where it is also marked by shadow 586, similarly with FIG. 5.

The determination of whether or not identified potential R peaks 659 in ECG portions 515, 516 meet a spuriousness criterion can be done in a number of ways. Examples are now described.

Figure 7:
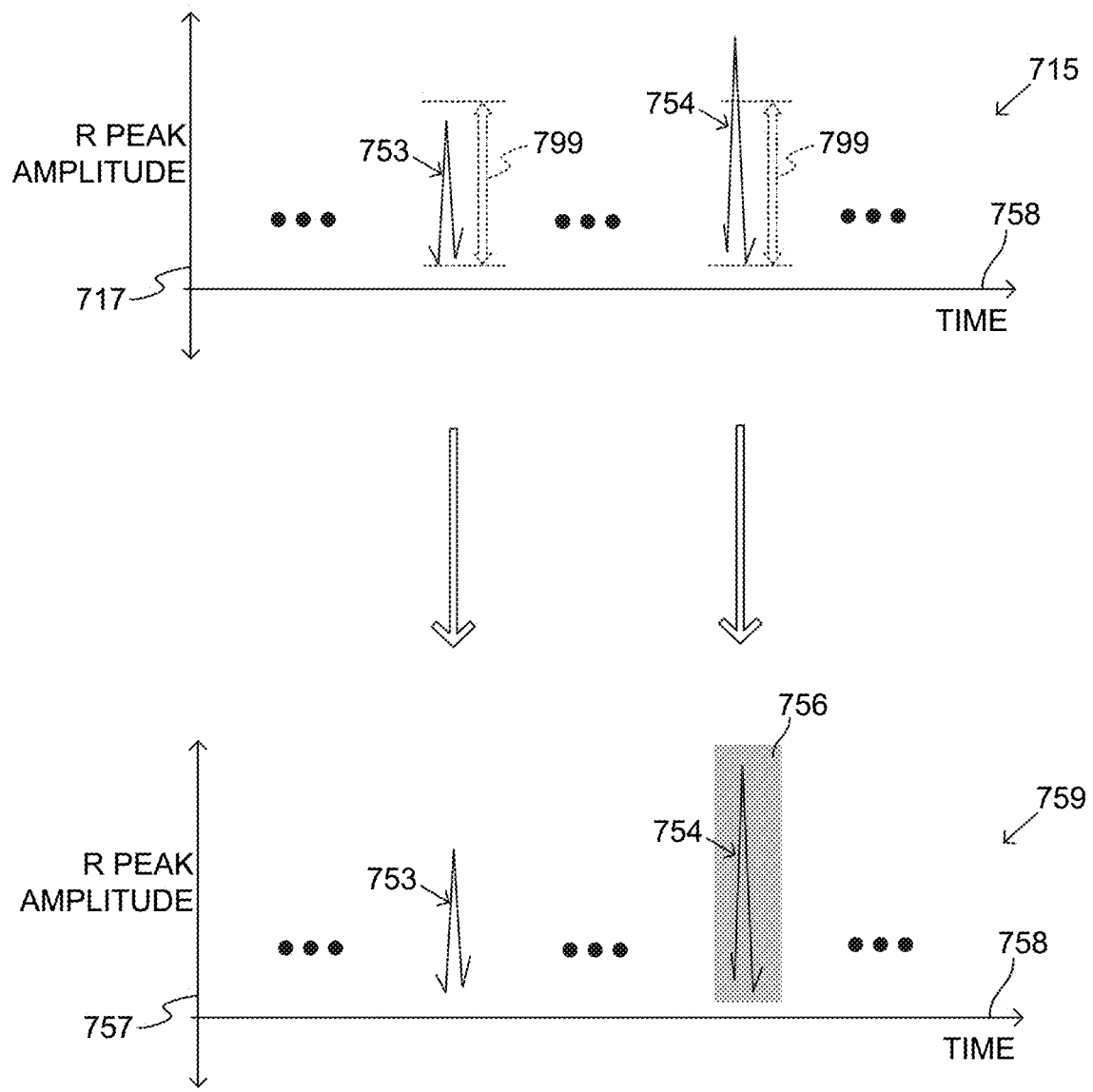
FIG. 7 shows time diagrams to illustrate an example of how a decision can be made as to whether or not identified potential R peaks in an ECG portion meet a first spuriousness criterion according to embodiments.

FIG. 7 has a time diagram 715 for illustrating a first spuriousness criterion. Diagram 715 has an R peak amplitude axis 717 and a time axis 758. Diagram 715 shows sample identified potential R peaks 753, 754, which could be as peaks 653, 654.

In some embodiments, an identified potential R peak 753, 754 meets the spuriousness criterion responsive to having an amplitude larger than a threshold amplitude 799. A suitable value for the threshold amplitude is 3 mV. Accordingly, identified potential R peaks with an amplitude less than threshold amplitude 799 do not meet the spuriousness criterion.

FIG. 7 also has another time diagram 759, for showing results similar to R peaks 659. Diagram 759 also has an R peak amplitude axis 757 and a time axis 758 that is repeated from diagram 715.

As can be seen, identified potential R peak 753 has an amplitude less than threshold amplitude 799, and therefore the spuriousness criterion is not met. Accordingly, identified potential R peak 753 is repeated in diagram 759 without being marked by a shadow, similarly with FIG. 6. However, identified potential R peak 754 has an amplitude larger than threshold amplitude 799, and therefore the spuriousness criterion is met. Accordingly, identified potential R peak 754 is repeated in diagram 759, where it is further marked by shadow 756, similarly with FIG. 6.

In some embodiments, the sensed ECG signal is filtered, and therefore the ECG portions filtered may be filtered as well. Filtering may take place, for example, by filter 325. Filter 325 may be a bandpass filter that passes frequencies between 2.75 Hz and 20 Hz. In such embodiments, all of what was written above may apply to the filtered ECG signal. In particular, an identified potential R peak in the certain filtered ECG portion may meet the spuriousness criterion responsive to having an amplitude larger than a threshold amplitude.

Figure 8:
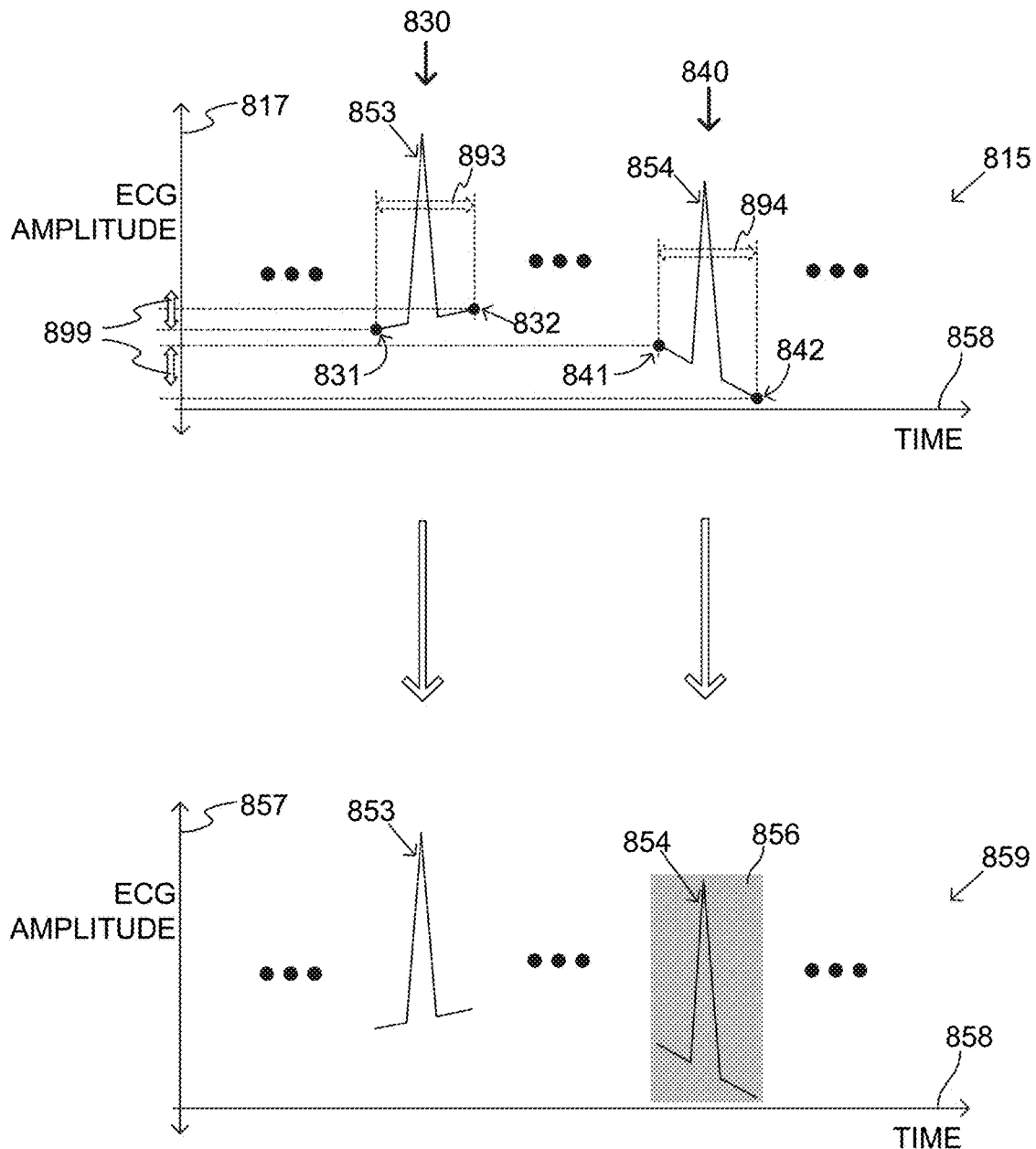
FIG. 8 shows time diagrams to illustrate an example of how a decision can be made as to whether or not identified potential R peaks in an ECG portion meet a second spuriousness criterion according to embodiments.

FIG. 8 has a time diagram 815 for illustrating a second spuriousness criterion. Diagram 815 has an ECG amplitude axis 817 and a time axis 858. Diagram 815 shows sample identified potential R peaks 853, 854, which could be as peaks 653, 654.

In some embodiments, ECG segments 830, 840 become defined so as to have time durations 893, 894 that include the respective identified potential R peaks 853, 854. In some embodiments, an identified potential R peak (853, 854) meets the spuriousness criterion responsive to a starting amplitude at the beginning of the ECG segment differing from an ending amplitude at the end of the ECG segment by more than a threshold baseline shift 899.

FIG. 8 also has another time diagram 859, for showing results similar to R peaks 659. Diagram 859 also has an ECG amplitude axis 857 and a time axis 858 that is repeated from diagram 815.

As can be seen, for identified potential R peak 853, the spuriousness criterion would be met if a starting amplitude at a beginning point 831 of ECG segment 830 differs from an ending amplitude at an end point 832 of ECG segment 830 by more than threshold baseline shift 899. Beginning point 831 and end point 832 are further shown projected onto vertical axis 817, from where it becomes apparent that their difference is smaller than threshold baseline shift 899. As such, the spuriousness criterion is not met for identified potential R peak 853. Accordingly, identified potential R peak 853 is repeated in diagram 859 without being marked by a shadow, similarly with FIG. 6.

As can be seen further, for identified potential R peak 854, the spuriousness criterion would be met if a starting amplitude at a beginning point 841 of ECG segment 840 differs from an ending amplitude at an end point 842 of ECG segment 840 by more than threshold baseline shift 899. Beginning point 841 and end point 842 are further shown projected onto vertical axis 817, from where it becomes apparent that their difference is larger than threshold baseline shift 899. As such, the spuriousness criterion is met for identified potential R peak 854. Accordingly, identified potential R peak 854 is repeated in diagram 859, where it is further marked by shadow 856, similarly with FIG. 6.

In some embodiments, a ratio of threshold baseline shift 899 over time durations 893, 894 of ECG segments 830, 840 is at least 5 mV/200 ms. Practically speaking, time duration 893 can be chosen to start 100 milliseconds (ms) prior to identified potential R peak 853, and end 100 ms after it. As such, time duration 893 would be 200 ms and threshold baseline shift 899 can be 5 mV.

As mentioned above, in some embodiments the ECG portions are defined as the identified potential R peaks in the sensed ECG signal. In such embodiments, the identified potential R peaks become marked responsive to meeting a spuriousness criterion. The spuriousness criterion can be as mentioned above, and described with reference to FIGS. 6-8. Then a noise fraction can be computed, of a number of the identified potential R peaks of the group over a total number of the identified potential R peaks of the group. Then the noise condition can be met responsive to the noise fraction exceeding a threshold noise fraction, as per the above, and similarly also with the quiet fraction.

Figure 9:
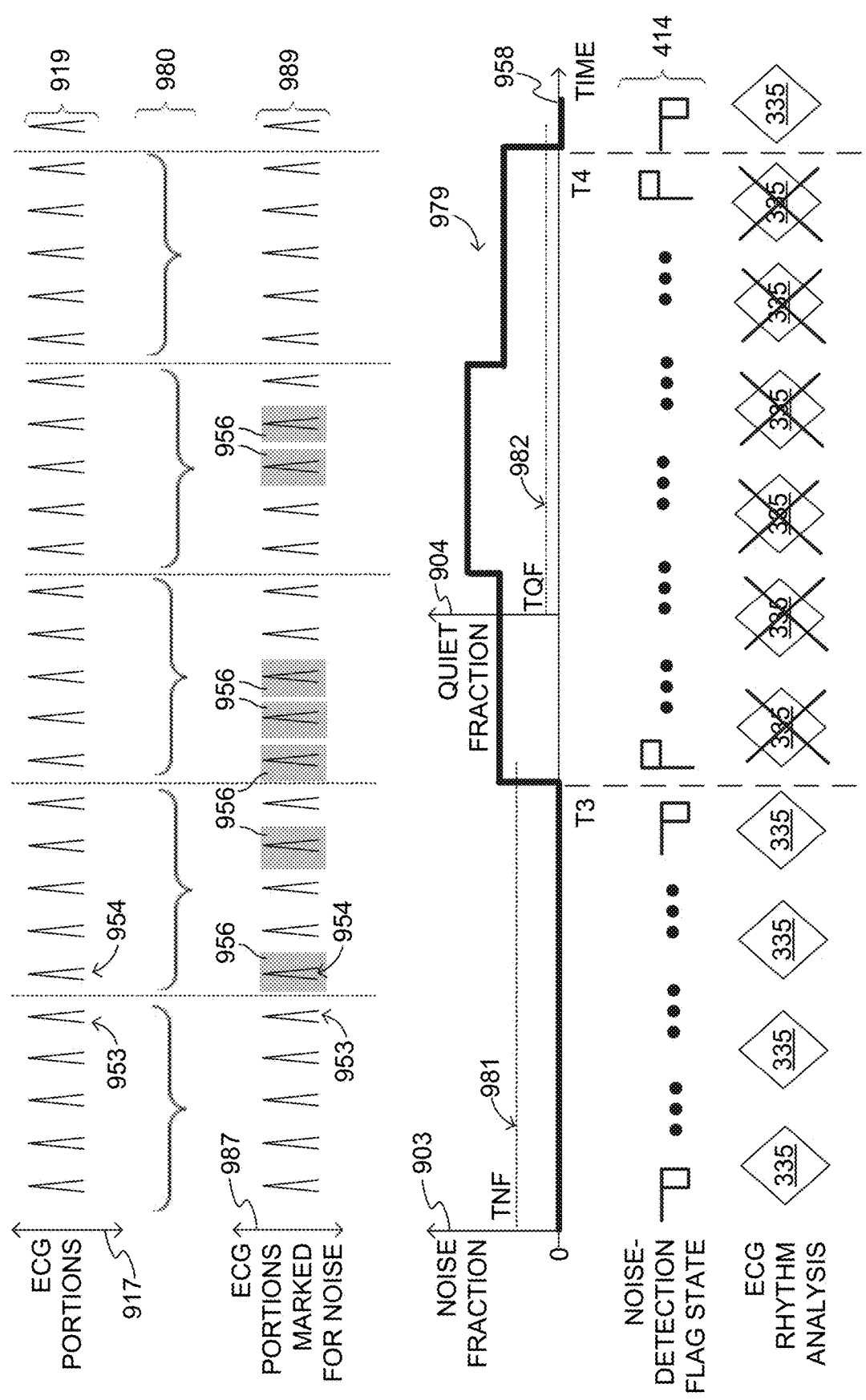
FIG. 9 repeats FIG. 5 for the specific embodiments where ECG portions are defined as peaks identified in the sensed ECG signal, and which could be R peaks of a QRS complex.

FIG. 9 shows sample time evolutions of a number of quantities according to embodiments, against a time axis 958. Sample ECG portions 919 are shown with reference to an ECG portions axis 917. It will be observed that ECG portions 919 are depicted as single peaks. Two sample such peaks 953, 954 are identified, which could be identified from the ECG signal as shown in FIG. 6 for peaks 653, 654. In addition, groupings 980 are shown, and what is written above about groupings 580 also applies. As such, a single group in this instance can be a collection of peaks detected in the sensed ECG signal, which can be R peaks of respective QRS complexes.

Below groupings 980, ECG portions 989 repeat ECG portions 919 next to a vertical axis 987. In addition, some of ECG portions 989 are shown marked with a shadow 956. For example ECG portion 954 is marked with a shadow 956, but ECG portion 953 is not. Such marking can be for those of ECG portions 989 that meet a spuriousness criterion.

Moreover, a diagram 979 shows the time evolution of a sample fraction using two vertical abscissa axes: a noise fraction axis 903, and then another a quiet fraction axis 904 that follows axis 903. A value of 0.3 for the threshold noise fraction is shown by a dotted line 981, and a time intercept TNF on axis 503. A plot of noise fraction 979 intersects dotted line 981 at time T3. A value for the threshold quiet fraction of 0.1 is shown by a dotted line 982, and a time intercept TQF on axis 904. The plot of noise fraction 979 intersects dotted line 982 at time T4. The remainder of FIG. 9 is similar to what was described above with reference to FIG. 5.

In the methods described above, each operation can be performed as an affirmative act or operation of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description.

Some technologies or techniques described in this document may be known. Even then, however, it does not necessarily follow that it is known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

In this description a single reference numeral may be used consistently to denote a single item, aspect, component, or process. Moreover, a further effort may have been made in the drafting of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that it can have one or more of this component or item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A wearable cardioverter defibrillator (WCD) system, comprising:
    a support structure configured to be worn by an ambulatory patient;
    an energy storage module configured to store an electrical charge;
    a discharge circuit coupled to the energy storage module;
    electrodes configured to sense an Electrocardiogram (ECG) signal of the patient;
    a processor configured to:
        set a noise-detected flag responsive to the sensed ECG signal meeting a High-Amplitude (H-A) noise criterion, and unset the noise-detected flag responsive to the sensed ECG signal meeting a High-Amplitude (H-A) quiet criterion, wherein the H-A noise criterion is met when a fraction of ECG portions in a group of ECG portions having a potential R peak exceeding a threshold amplitude is greater than a threshold fraction, and the H-A quiet criterion is met when the H-A noise criterion is no longer met;
        determine, from the sensed ECG signal, whether a shock criterion is met, and control, responsive to the shock criterion being met and the noise-detected flag being unset, the discharge circuit to discharge the stored electrical charge through the patient while the support structure is worn by the patient to deliver a shock to the patient, wherein the discharge circuit is controlled to not discharge when the noise-detected flag is set even when it is determined that the shock criterion is met.

2. The WCD system of claim 1, in which
the noise-detected flag becomes unset responsive to the noise-detected flag having been set for a tolerance time.

3. The WCD system of claim 2, in which
the tolerance time is at least 0.5 minutes.

4. The WCD system of claim 1, in which
it is not determined whether the shock criterion is met when the noise-detected flag is set.

5. The WCD system of claim 1, further comprising:
a user interface configured to output an alert responsive to the noise-detected flag being set.

6. The WCD system of claim 5, in which
the alert is output further responsive to the noise-detected flag having been set for a tolerance time.

7. The WCD system of claim 6, in which
the tolerance time is at least 0.5 minutes.

8. The WCD system of claim 5, in which
the noise-detected flag becomes unset responsive to outputting the alert.

9. The WCD system of claim 1, in which
ECG portions of the sensed ECG signal are defined, and
the H-A noise criterion is met responsive to a group of the most recent ECG portions meeting a noise condition.

10. The WCD system of claim 9, in which
if the H-A noise criterion is not met, it is determined whether a shock criterion is met only from the ECG portions that do not meet the noise condition.

11. The WCD system of claim 9, in which
ECG portions of the group become marked responsive to meeting a noisiness criterion,
a noise fraction is computed of a number of the marked ECG portions of the group over a total number of the ECG portions of the group, and
the noise condition is met responsive to the noise fraction exceeding a threshold noise fraction.

12. The WCD system of claim 11, in which
potential R peaks of QRS complexes are identified in a certain ECG portion of the group,
the identified potential R peaks in the certain ECG portion that meet a spuriousness criterion are deemed invalid,
a validity ratio is defined for the certain ECG portion by a number of the potential R peaks in the certain ECG portion that are deemed invalid over a total number of the identified potential R peaks in the certain ECG portion, and
the certain ECG portion meets the noisiness criterion responsive to the validity ratio exceeding a threshold validity ratio.

13. The WCD system of claim 12, in which
an identified potential R peak in the certain ECG portion meets the spuriousness criterion responsive to having an amplitude larger than a threshold amplitude.

14. The WCD system of claim 13, in which
the certain ECG portion is filtered, and
an identified potential R peak in the certain filtered ECG portion meets the spuriousness criterion responsive to having an amplitude larger than a threshold amplitude.

15. The WCD system of claim 12, in which
an ECG segment is defined to have a time duration that includes a certain one of the identified potential R peaks in the certain ECG portion, and
the certain identified potential R peak meets the spuriousness criterion responsive to a starting amplitude at the beginning of the ECG segment differing from an ending amplitude at the end of the ECG segment by more than a threshold baseline shift.

16. The WCD system of claim 9, in which
potential R peaks of QRS complexes are identified in the sensed ECG signal, and
the ECG portions are defined as the identified potential R peaks.

17. The WCD system of claim 16, in which
the identified potential R peaks are marked responsive to meeting a spuriousness criterion,
a noise fraction is computed from a number of the identified potential R peaks of the group over a total number of the identified potential R peaks of the group, and
the noise condition is met responsive to the noise fraction exceeding a threshold noise fraction.

18. The WCD system of claim 17, in which
an identified potential R peak meets the spuriousness criterion responsive to having an amplitude larger than a threshold amplitude.

19. The WCD system of claim 18, in which
the sensed ECG signal is filtered, an
an identified potential R peak meets the spuriousness criterion responsive to having an amplitude larger than a threshold amplitude.

20. The WCD system of claim 17, in which
an ECG segment becomes defined to have a time duration that includes a certain one of the identified potential R peaks in the certain ECG portion, and
the certain identified potential R peak meets the spuriousness criterion responsive to a starting amplitude at the beginning of the ECG segment differing from an ending amplitude at the end of the ECG segment by more than a threshold baseline shift.

21. The WCD system of claim 9, in which
the H-A quiet criterion is met responsive to another group of the most recent ECG portions not meeting the H-A noise condition, at least one ECG portion of the other group occurring after at least one ECG portion of the group.

22. The WCD system of claim 9, in which
the H-A quiet criterion is met responsive to another group of the most recent ECG portions meeting a quiet condition, at least one ECG portion of the other group occurring after at least one ECG portion of the group.

23. The WCD system of claim 22, in which
ECG portions of the group become marked responsive to meeting a noisiness criterion,
a quiet fraction is computed of a number of the marked ECG portions of the group over a total number of the ECG portions of the group, and
the quiet condition is met responsive to the quiet fraction being less than a threshold quiet fraction.

24. The WCD system of claim 23, in which
potential R peaks of QRS complexes are identified in a certain ECG portion of the other group,
the identified potential R peaks in the certain ECG portion that meet a spuriousness criterion are deemed invalid,
a validity ratio is defined for the certain ECG portion by a number of the potential R peaks in the certain ECG portion that are deemed invalid over a total number of the identified potential R peaks in the certain ECG portion, and the certain ECG portion meets the noisiness criterion responsive to the validity ratio exceeding a threshold validity ratio.

25. The WCD system of claim 24, in which an identified potential R peak in the certain ECG portion meets the spuriousness criterion responsive to having an amplitude larger than a threshold amplitude.

26. The WCD system of claim 25, in which the certain ECG portion is filtered, and an identified potential R peak in the certain filtered ECG portion meets the spuriousness criterion responsive to having an amplitude larger than a threshold amplitude.

27. The WCD system of claim 24, in which an ECG segment becomes defined to have a time duration that includes a certain one of the identified potential R peaks in the certain ECG portion, and the certain identified potential R peak meets the spuriousness criterion responsive to a starting amplitude at the beginning of the ECG segment differing from an ending amplitude at the end of the ECG segment by more than a threshold baseline shift.

* * * * *